United States Patent [19]

Brewster

[11] 4,201,683

[45] May 6, 1980

[54] ALKANOL SOLUTIONS OF ORGANO MOLYBDENUM COMPLEXES AS FRICTION REDUCING ANTIWEAR ADDITIVES

[75] Inventor: Philip W. Brewster, Camlachie, Canada

[73] Assignee: Exxon Research & Engineering Co., Florham Park, N.J.

[21] Appl. No.: 898,839

[22] Filed: Apr. 21, 1978

[51] Int. Cl.$^2$ .................... C10M 1/38; C10M 1/48; C10M 1/54

[52] U.S. Cl. .................... 252/32.7 E; 44/68; 252/42.7; 252/49.7; 260/429 D; 260/429 R

[58] Field of Search .................. 252/42.7, 32.7 E; 260/429 R, 429 D; 44/68

[56] References Cited

U.S. PATENT DOCUMENTS

| | | | |
|---|---|---|---|
| 2,270,183 | 1/1942 | Cook | 252/42.7 |
| 3,047,500 | 7/1962 | Matson | 252/42.7 |
| 3,184,410 | 5/1965 | Bretherick | 252/42.7 |
| 3,356,702 | 12/1969 | Farmer et al. | 252/42.7 |
| 3,541,014 | 11/1970 | LeSuer | 252/42.7 |
| 3,636,023 | 1/1972 | Murray et al. | 260/429 D |
| 4,011,167 | 3/1977 | Chibnik | 252/42.7 |
| 4,121,025 | 10/1978 | Scott | 260/45.75 R |

FOREIGN PATENT DOCUMENTS 882295  11/1961  United Kingdom .

*Primary Examiner*—Arthur P. Demers
*Attorney, Agent, or Firm*—Roland A. Dexter

[57] ABSTRACT

A solution of a hydrocarbon-soluble organo molybdenum complex obtained as the solution reaction product of a hydrocarbyl substituted thio-bis-phenol, e.g. 2,2$^1$-thio-bis (4-iso-nonyl phenol), with a molybdenum compound, e.g. molybdic oxide and an amine such as ethylene diamine in a solvent of a $C_5$–$C_{50}$ alkanol, e.g. tridecyl alcohol is a useful hydrocarbon additive, particularly when used in combination with an oil-soluble sulfur donor, e.g. a metal dialkyl dithiophosphate which provides an additive combination for lubricants and fuels whereby the resulting lubricating composition appears to exhibit an improved antifriction property.

12 Claims, No Drawings

ALKANOL SOLUTIONS OF ORGANO MOLYBDENUM COMPLEXES AS FRICTION REDUCING ANTIWEAR ADDITIVES

BACKGROUND OF THE INVENTION

The present invention relates to alkanol solutions of hydrocarbon-soluble molybdenum complexes of thio-bis-phenols, their method of preparation and their utility as an additive for hydrocarbon compositions such as gasoline, fuel oil and lubricating oils including greases, industrial oils, gear oils and lubricants for engines and other equipment having moving parts operating under boundary lubricating conditions.

There are many instances, as is well known, particularly under "Boundary Lubrication" conditions where two rubbing surfaces must be lubricated, or otherwise protected, so as to prevent wear and to insure continued movement. Moreover, where, as in most cases, friction between the two surfaces will increase the power required to effect movement and where the movement is an integral part of an energy conversion system, it is most desirable to effect the lubrication in a manner which will minimize this friction. As is also well known, both wear and friction can be reduced, with various degrees of success, through the addition of a suitable additive or combination thereof, to a natural or synthetic lubricant. Similarly, continued movement can be insured, again with varying degrees of success, through the addition of one or more appropriate additives.

While there are many known additives which may be classified as antiwear, antifriction and extreme pressure agents and some may in fact satisfy more than one of these functions as well as provide other useful functions, it is also known that many of these additives act in a different physical or chemical manner and often compete with one another, e.g. they may compete for the surface of the moving metal parts which are subjected to lubrication. Accordingly, extreme care must be exercised in the selection of these additives to insure compatibility and effectiveness.

The metal dihydrocarbyl dithiophosphates are one of the additives which are known to exhibit antioxidant and antiwear properties. The most commonly used additives of this class are the zinc dialkyl dithiophosphates which are conventionally used in lubricant compositions. While such zinc compounds afford excellent oxidation resistances and exhibit superior antiwear properties, it has heretofore been believed that the same increases or significantly limits the ability to decrease friction between moving surfaces. As a result, compositions containing zinc dialkyl dithiophosphates were not believed to provide the most desirable lubricity and, in turn, it was believed that use of compositions containing the same would lead to significant energy losses in overcoming friction even when antifriction agents are included in the composition.

Known ways to solve the problem of energy losses due to high friction, e.g. in crankcase motor oils include the use of synthetic ester base oils which are expensive and the use of insoluble molybdenum sulfides which have the disadvantage of giving the oil composition a black or hazy appearance.

Other types of molybdenum compounds taught to be useful in lubricating oils include the alkyl esters of molybdic acid as corrosion inhibitors (see U.S. Pat. No. 2,805,997) and nitrogenous thiomolybdates as metal antiwear additives which are said to function by providing a coating of reduced coefficient of friction (see U.S. Pat. No. 2,938,869).

Similarly, antifriction agents or oiliness or lubricity agents as the same are often referred to in the prior art, function by forming a coating on the surface of the moving metal parts. As in the case of antiwear agents, however, the coating bonds are, generally, effected physically, rather than chemically, and, indeed, the bonding between an antifriction agent and the surface is, generally, weaker than the bond formed between an antiwear agent and the metal surface.

In light of the foregoing, the need for improved lubricating compositions, particularly for engine lubricating oils, that will permit operation of moving parts under boundary conditions with reduced friction is believed to be readily apparent. Similarly, the need for such a composition that can include conventional base oils and other conventional additives such as ashless dispersants, detergents, antioxidants (e.g. hindered phenols), demulsifiers (e.g. up to about 0.01 wt.% alkanols—see U.S. Pat. No. 3,591,497, col. 1, lines 50–58), seal swellants (e.g. $C_8$–$C_{13}$ alkanols—see U.S. Pat. No. 3,389,088), V.I. improvers, etc., and can be used without the loss of other desirable lubricant properties, particularly those provided by zinc dialkyl dithiophosphates, is also readily apparent.

SUMMARY OF THE INVENTION

In U.S. patent application Ser. No. 843,964 filed Oct. 20, 1977, and of common assignee, there is a teaching of a class of organo molybdenum complexes believed to be represented by the following formula I:

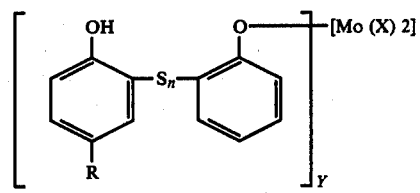

where n is 1–3, Y is 1–2, X is selected from sulphur or oxygen and R is a substantially hydrocarbyl group containing from 1 to 50, preferably 12 to 28, carbon atoms and X is selected from sulphur or oxygen. These complexes are produced by the solution reaction of a thio-bis-phenol, a source of molybdenum and an amine in a mineral oil solvent which are reported as therein useful friction-reducing additives for lubricants and fuels. It has now been discovered that said complexes containing from about 0.5 to about 5, preferably 1 to 2.5, optimally 1.4, wt.% of nitrogen are more readily produced in quantitative yields at lower temperatures and with a broader spectrum of amines (all with respect to said teaching) when their preparative reaction is carried out in an alkanol solvent wherein said alkanol is a $C_5$ to $C_{50}$, preferably $C_8$ to $C_{18}$, optimally $C_{13}$ Oxo alkanol.

The amine reactants include ammonia, simple amines such as $C_6$–$C_{30}$ alkyl amines, alkylene polyamines such as ethylene diamine (preferred) and diethylene triamine, akanolamines such as ethanolamine, ethoxylated derivatives of alkylene diamines such as hydroxyethyl ethylene diamine, urea and ureides. When said complex is introduced into the lubricating oil in combination with said phenol, e.g. as the solution of said reaction, the modified lubricating oil exhibits of dynamic coefficient of friction markedly reduced relative to that obtained with the addition of only a common amount of organo molybdenum complex.

In accordance with the present invention, the foregoing and other objects and advantages are accomplished with a hydrocarbon composition comprising a major portion of a hydrocarbon, e.g. a lubricating oil and at least a friction reducing amount of a solution of said organo molybdenum complex in a $C_5$–$C_{50}$ alkanol solvent and preferably a lubricity enhancing combination of: (a) said organo molybdenum complex; (b) said $C_5$ to $C_{50}$ alkanol; and, (c) an oil-soluble sulfur donor, preferably zinc dialkyl dithiophosphate, and if desired, at least a sludge-dispersing amount of an oil-soluble dispersant, e.g. an ashless dispersant and at least a rust-inhibiting amount of a rust inhibitor. In practice, the lubricity enhancing combination is present in an amount sufficient to provide from about 0.005 to 0.2, preferably 0.03 to 0.15, optimally about 0.1, wt.% molybdenum, at least about 0.25, e.g. 0.25 to 1, wt.% sulfur donor and from 0.25 to 5 wt.% $C_5$–$C_{50}$ alkanol, all weight percent being based on the total weight of the hydrocarbon composition such as lubricating oil or fuel.

DETAILED DESCRIPTION OF THE INVENTION

OIL-SOLUBLE ORGANO MOLYBDENUM COMPOUND

The hydrocarbon-soluble molybdenum complexes are believed to be derived from a thio-bis-phenol as shown in Formula I. The R group of said Formula I as defined is substantially hydrocarbyl and thus is alkyl; aryl, aralkyl, cycloalkyl, or alkaryl; however, the hydrocarbyl group may contain prior substituents such as amino, aminoalkyl, hydroxy, hydroxyalkyl, halo, mercapto, keto, phosphinyl, phosphoryl, thiophosphoryl and dithiophosphoryl radicals.

Specific examples of the R group include methyl, ethyl, propyl, isopropyl, isobutyl, n-butyl, sec-butyl, tert-butyl, n-hexyl, heptyl, octyl, nonyl-decyl, dodecyl, tridecyl, heptadecyl, octadecyl, polyisobutyl, polypropyl, etc.

The organic molybdenum complexes are the reaction product of a thio-bis-phenol, an amine and molybdenum. The aforesaid thio-bis-phenols can be characterized by Formula II.

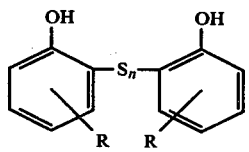

wherein R and n are each the same as previously described with R preferably para to the hydroxyl substituent. These thio-bis-phenols are readily produced from the reaction of alkyl phenols and a source of sulfur, e.g. chemical sulfur or sulfur halides. The alkyl phenols are readily produced by alkylation of a phenol with an olefin, e.g. nonene, in presence of an alkylation catalyst.

A particularly useful reactant for the preparation of the molybdenum complex can be characterized by Formula III.

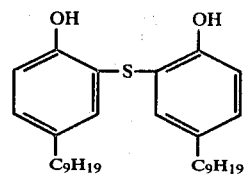

The source of molybdenum is a molybdenum containing compound capable of reacting with the thio-bis-phenol to provide a molybdenum complex containing from about 0.5 to 20, preferably 2 to 10, optimally about 5 wt.% molybdenum based on the total weight of said complex. The sources of molybdenum include molybdic trioxide (preferred) also known as molybdic anhydride, ammonium thiomolybdate, ammonium bismolybdate, molybdenum halides, and ammonium heptamolybdate tetrahydrate.

The organo molybdenum complex is substantially the product of a solution reaction between 1–2 moles thio-bis-phenol, 1 mole of molybdenum and 1–2 moles of an amine. The reaction is readily carried out by reaction at an elevated temperature of from 135° C. to 225° C., preferably 160° C. to 190° C. optimally 175° C. to accelerate said reaction and remove the water of reaction. The reaction is carried out in a $C_8$ to $C_{50}$ alkanol, preferably $C_8$–$C_{18}$ alkanol, optimally tridecyl alcohol. The reaction is carried out over a period of from about 4 to 20, preferably 6 to 12, hours in order to suitably stabilize the complex and for removal of the water of reaction as by nitrogen sparging or distillation at atmospheric or reduced pressure.

AMINES

The amine reactants broadly contain from 1 to 5, preferably 2, nitrogens and from 0 to 60, preferably 2 to 20 carbons. The preferred amines are of the class consisting of: $C_6$–$C_{30}$ alkyl amines such as n-octyl amine and dodecyl amine; alkylene polyamines which can be represented by the general formula $NH_2(CH_2)_n$—$[NH(CH_2)_n]_m$—$NH_2$ wherein n is 2 to 3 and m is a number from 0 to 3 including ethylene diamine, diethylene triamine, tetraethylene pentamine and mixtures of such polyamines formed from the reaction of ethylene dichloride and ammonia; alkanolamines such as ethanolamine and diethanolamine; ethoxylated derivatives of alkylene polyamine such as hydroxyethyl ethylenediamine and the reaction product of alkylene oxides such as an ethylene oxide or propylene oxide with polyamines e.g. dinitrilo tetraethanol; urea and ureides such as ethylurea.

Carrying out the organo molybdenum complexing reaction in a $C_5$–$C_{50}$, preferably $C_8$–$C_{18}$, optimally $C_{13}$, alkanol solvent in an amount ranging from about 0.25 to 5, preferably 1, parts by weight of alkanol per part by weight of organo molybdenum complex product provides a number of benefits over a reaction without solvent or in a light aromatic solvent such as toluene or a ligh hydrocarbon oil, e.g. mineral oil including: a faster reaction time; completion of reaction to a stabilized molybdenum complex at a lower temperature; faster and simpler filtration of the reaction product solution; and, an additive product solution which when added to lubricating oil provides enhanced friction reduction (as seen from the subsequent Table I.).

ALKANOLS

The $C_5$ to $C_{50}$, preferably $C_8$ to $C_{18}$, optimally $C_{13}$, alkanols useful as solvents for the organo molybdenum complexing reaction are in generally commercially available aliphatic alcohols which can be straight or branched chain. Among these alcohols useful in preparing said complexes are amyl alcohol, hexanol, heptanol, etc., through pentacontanol with the preferred alcohols being octanol through octadecanol. A highly suitable source of alcohols are the Oxo alcohols which are prepared in a two-stage reaction as has been described in U.S. Pat. No. 2,327,066. The first stage of the Oxo process involves reacting olefins, such as polymers and copolymers of $C_3$ and $C_4$ monoolefins, with carbon monoxide and hydrogen at temperatures about 150° to 200° C. and pressures of about 30 to 400 atmospheres in the presence of a suitable catalyst to form a mixture of aldehydes having one carbon atom more than the olefin. In the second stage, the aldehyde mixture is hydrogenated, to form an isomeric mixture of highly branched chain primary alcohols which is recovered by distillation. Particularly, suitable as a reaction solvent for this invention is tridecyl Oxo alcohol.

The $C_5$ to $C_{50}$ alkanols are usefully present in the hydrocarbon composition in an amount of from about 0.25 to 5, preferably 1, parts by weight per part by weight of said organo molybdenum complex.

SULFUR DONORS

The $C_5$–$C_{50}$ alkyl phenol solutions of the hydrocarbon-soluble organo molybdenum complexes provide enhanced lubricity in lubricating oils when used in combination with an active sulfur donor which can be defined as a compound which when used in admixture with the organo molybdenum complex reduces the coefficient of friction at least about 10% relative to that provided by the complex alone. The active sulfur donor is present in an amount of from about 0.1 to 10, preferably 0.2 to 2, parts by weight per part by weight of molybdenum complex.

Illustrative of active sulfur donors are metal dihydrocarbyl dithiophosphates and the corresponding precursor esters, phosphosulfurized pinenes, sulfurized olefins and hydrocarbons, sulfurized fatty esters and sulfurized alkyl phenols.

Preferred are the zinc dihydrocarbyl dithiophosphates which are salts of dihydrocarbyl esters of dithiophosphoric acids and may be represented by the following formula:

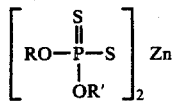

wherein R and R' may be the same or different hydrocarbyl radicals containing from 1 to 18 and preferably 2 to 12 carbon atoms and including radicals such as alkyl, alkenyl, aryl, aralkyl, alkaryl and cycloaliphatic radicals. Particularly preferred as R and R' groups are alkyl groups of 2 to 8 carbon atoms. Thus, the radicals may, for example, be ethyl, n-propyl, i-propyl, n-butyl, i-butyl, sec-butyl, tert-butyl, amyl n-hexyl, i-hexyl, n-heptyl, n-octyl, decyl, dodecyl, octadecyl, 2-ethylhexyl, phenyl, butylphenyl, cyclohexyl, methylcyclopentyl, propenyl, butenyl, etc. In order to obtan oil solubility, the total number of carbon atoms in the dithiophosphoric acid will average about 5 or greater.

The zinc dihydrocarbyl dithiophosphates which are useful as the coadditive, i.e. sulfur donor of the present invention may be prepared in accordance with known techniques by first esterifying a dithiophosphoric acid usually by reaction of an alcohol or phenol with $P_2S_5$ and then neutralizing the dithiophosphoric acid ester with a suitable zinc compound such as zinc oxide.

In general, the zinc dihydrocarbyl dithiophosphate will be used in the lubricating composition at a concentration within the range of about 0.01 to about 5 parts by weight per 100 parts of lubricating oil and preferably from about 0.5 to about 1.5. This is adequate for sulfur donation whereby the lubricity enhancement of the lubricating oil composition by the coadditive combination is realized.

As noted earlier, an equally suitable active sulfur donor is the dihydrocarbyl esters of dithiophosphoric acid which may be represented by the formula:

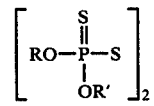

where R and R'' are as previously defined. Particularly useful is the dibutylphenyl dithiophosphate.

The phosphorosulfurized terpenes as represented by pinene, dipenene, allo-ocimene, etc., are another group of dithiophosphate diesters which are active sulfur donors. Of the terpenes, the bicyclic pinene is preferred. The phosphosulfurized terpene is readily obtained by reaction of about one mole of diester of thiophosphoric acid and one mole of pinene at a temperature of at least 100° C., e.g. 100° C. to 200° C. The preferred active sulfur donor can be characterized as the bornyl ester of dihydrocarbyl ($C_2$–$C_{20}$) dithiophosphoric acids (as shown in U.S. Pat. No. 2,689,258).

The sulfurized olefins and hydrocarbons are further esters of thiophosphoric acids which are useful sulfur donors. These esters are achieved by reaction with olefins such as ethylene, propylene, isobutylene, decene, dodecene, octadecene, etc., olefin polymers of molecular weight ranging from 100 to 50,000 such as ethylene, propylene, isobutylene, etc., aromatics such as benzene, naphthylene, toluene, xylene, etc., petroleum fractions and condensation products of halogenated aliphatic hydrocarbons with aromatic compounds, e.g. wax naphthalene (see U.S. Pat. No. 2,804,431).

The sulfurized fatty esters are another subclass of esters which are active sulfur donors. These products are readily obtained from the reaction of $P_2S_5$ and aliphatic alcohols usefully having from about 8 to 22 carbons obtained from natural sources including linoleic, palmolitic, behenic, stearic, palmitic, lauric, capric, etc., as well as mixtures obtained from vegetable and animal oils such as tall oil.

The sulfurized alkyl phenols are generally $C_4$ to $C_{20}$ alkyl phenol sulfides. These sulfurized alkyl phenols are readily produced by sulfurizing an alkyl phenol with a sulfur halide or elemental sulfur.

OTHER ADDITIVES FOR LUBRICATING COMPOSITIONS

In addition to the organo molybdenum complex, alkanol and active sulfur donor, the lubricating oil composition may contain other well-known lubricating oil additives to provide trouble-free operation of the lubricated equipment, such as ashless dispersants, metallic detergents, supplemental oxidation and corrosion inhibitors, extreme pressure agents, rust inhibitors, pour point depressants, viscosity index improvers, etc.

1. ASHLESS DISPERSANTS

As used herein, the terminology "ashless dispersant" is intended to describe the now well-known class of non-metal-containing oil-soluble polymeric additives or the acyl derivatives of relatively high molecular weight carboxylic acids which are capable of dispersing contaminants and the like in hydrocarbons such as lubricating oils. The carboxylic acids may be mono- or polycarboxylic acids and they are generally characterized by substantially hydrocarbon constituents containing an average of 50 to 250 aliphatic carbon atoms.

A preferred class of ashless dispersants are the nitrogen-containing dispersant additives which are generally known in the art as sludge dispersants for crankcase motor oils. These dispersants include mineral oil-soluble salts, amides, imides and esters made from high molecular weight mono- and dicarboxylic acids (and where they exist the corresponding acid anhydrides) and various amines of nitrogen-containing materials having amino nitrogen or heterocyclic nitrogen and at least one amido or hydroxy group capable of salt, amide, imide or ester formation. Usually, these dispersants are made by condensing a monocarboxylic acid or a dicarboxylic acid or anhydride, preferably a succinic acid producing material such as alkenyl succinic anhydride, with an amine or alkylene polyamine. Usually, the molar ratio of acid or anhydride to amine is between 1:1 to 5:1, e.g. 1 mole of $C_{10}$–$C_{100}$ polyisobutenyl succinic anhydride to 2 moles of tetraethylene pentamine.

Primarily because of its ready availability and low cost, the hydrocarbon portion of the mono-, or dicarboxylic acid or anhydride is preferably derived from a polymer of a $C_2$ to $C_5$ monoolefin, said polymer generally having between 50 and 250 carbon atoms. A particularly preferred polymer is polyisobutylene.

Polyalkyleneamines are usually used to make the non-metal-containing dispersant. These polyalkyleneamines include those represented by the general formula:

$NH_2(CH_2)_n$—$[NH(CH_2)_n]_m$—$NH_2$ wherein n is 2 to 3 and m is a number from 0 to 10. Specific compounds coming within the formula include diethylenetriamine, tetraethylenepentamine, dipropylenetriamine, octaethylenenonamine, and tetrapropylenepentamine; N,N-di-(2-aminoethyl) ethylenediamine may also be used. Other aliphatic polyamino compounds that may be used are N-amino-alkylpiperazines, e.g. N-(2-aminoethyl) piperazine. Mixtures of alkylene polyamines approximating tetraethylene pentamine are commercially available, e.g. Dow E-100 sold by Dow Chemical Company of Midland, Michigan.

Representative dispersants are formed by reacting about one molar amount of polyisobutenyl succinic anhydride with from about one to about two molar amounts of tetraethylene pentamine or with from about 0.5 to 1 moles of a polyol, e.g. pentaerythritol.

It is possible to modify the ashless dispersants generally by the addition of metals such as boron in order to enhance the dispersancy of the additive. This is readily accomplished by adding boric acid to the reaction mixture after the imidation or esterification is substantially complete and heating the mixture at temperatures of 100° to 150° C. for a few hours.

2. OTHER ADDITIVES

Detergents useful in conjunction with dispersants, preferably the ashless type, include normal, basic or overbased metal, e.g. calcium, magnesium, etc., salts of petroleum naphthenic acids, petroleum sulfonic acids, alkyl benzene sulfonic acids, oil-soluble fatty acids, alkyl salicyclic acids, alkylene-bis-phenols, and hydrolyzed phosphorosulfurized polyolefins.

Oxidation inhibitors include hindered phenols, e.g. 2,6-ditert. butyl para-cresol, amines, sulfurized phenols and alkyl phenothiazines.

Pour point depressants include wax alkylated aromatic hydrocarbons, olefin polymers and copolymers, acrylate and methacrylate polymers and copolymers.

Viscosity Index Improvers include olefin polymers such as polybutene, ethylene-propylene copolymers, hydrogenated polymers and copolymers and terpolymers of styrene with isoprene and/or butadiene, polymers of alkyl acrylates or alkyl methacrylates, copolymers of alkyl methacrylates with N-vinyl pyrollidone or dimethylaminoalkyl methacrylate, post-grafted polymers of ethylenepropylene with an active monomer such as maleic anhydride which may be further reacted with an alcohol or an alkylene polyamine, styrene/maleic anhydride polymers post-reacted with alcohols and amines, etc.

The hydrocarbons in which the additive combination of the invention is most effective are mineral oils having a viscosity as measured by ASTM D-445 of from about 2 to 40, preferably 5 to 20 centistokes at 99° C.

If the additive combination of oil-soluble organo molybdenum complex $C_5$–$C_{20}$ alkanol and active sulfur donor are used as an additive concentrate, the concentrate may consist essentially of from about 5 to 95% of the additive combination, the remainder being an additional hydrocarbon solvent such as kerosene, mineral oil, a naphtha and the like or a $C_5$–$C_{50}$ alkyl phenol as disclosed in my copending application Ser. No. 898,769 filed on Apr. 21, 1978. The preferred concentrate contains about 40 to 90% of the additive combination in a second solvent of mineral oil.

Whether the organo molybdenum complex-alkanol solution is used alone or in combination with an active sulfur donor, its concentration may vary appreciably with the particular hydrocarbon. For example, when said molybdenum complex-alkanol solution is used alone in a fuel such as gasoline, the concentration of the complex ranges from 10 to 1,000, preferably 20 to 50 weight parts per million based on the total weight of the fuel composition, whereas in a lubricant, it is used in combination with the active sulfur donor, which three-component combination then ranges from about 0.5 to 5, preferably 1 to 3 wt.% based on the total weight of the lubricating oil.

The invention will be further understood by reference to the following Examples which illustrate a preferred form of the invention and compares the same with different, though similar compositions.

The following Examples illustrate more clearly the compositions of the present invention. However, these illustrations are not to be interpreted as specific limitations on this invention.

EXAMPLE 1

Nonyl phenol sulfide (183 g) as ECA 9001, Solvent Neutral 150 mineral oil (183 g) and molybdic trioxide (28.1 g) as an undensified grade obtained from Climax Molybdenum Company, Fort Madison, Wisconsin were stirred together and then raised in temperature to 94° C. at which time ethylene diamine (23.4 g) was thereafter slowly added over a 20-minute period. The temperature was raised with stirring to 121° C. over 0.6 hour. While stirring at this temperature, the volatiles including water and ammonia were removed by gentle nitrogen sparging for 18 hours. After filtration, the resulting product solution, useful as a lubricating oil additive, had a viscosity of 177 S.U.S. @ 100° C. and was black in color and contained about 4.3 wt.% molybdenum and 1.9 wt.% nitrogen. ECA 9001, a 70 wt.% active mineral solution of di-($C_9$ average) nonyl phenol sulfide is commercially available from Exxon Chemical Company, Houston, Texas.

This was an organo metallic complex prepared according to the teachings of said copending application Ser. No. 843,964 using a mineral oil solvent for the reaction medium. Filtration through a steam-heated Buchner funnel holding a ¼" precoat of Celite 535 took in excess of 1 hr. Exposure of the product solution to about 150° C. for 3 hours reduced its nitrogen content to 1.43 wt.% and appeared to evolve ammonia during said 3 hours.

EXAMPLE 2

The procedure of Example 1 was followed except that the mineral oil was replaced by: 183 g of tridecyl Oxo alcohol; use of densified $MoO_3$; going to 149° C. over a 2-hour period while adding the ethylene diamine; and reacting by raising the temperature to 177° C. after 1 hour followed by a temperature decrease to 149° C. where it was held for 2 hours. The resulting filtered product solution (the filtration of which took less than 10 minutes to fully filter) analyzed for 4.72 wt.% molybdenum.

EXAMPLE 3

The filtered product solution of Example 2 was thereafter heated under nitrogen sparging at 177° C. for 3 hours.

EXAMPLE 4

As earlier noted before, a preferred process provides for from 6 to 12 hours exposure of the reaction medium to a temperature about 175° C., usefully 160° C. to 190° C. This is shown in a procedure in which 183 weight parts of nonylphenol sulfide (e.g. ECA 9001) are admixed with 183 weight parts of tridecyl Oxo alcohol and heated toward 105° C. during which time 28.1 weight parts of molybdic trioxide are added. When 105° C. is reached 23.4 weight parts of ethylene diamine is slowly added over a 30-minute period. Thereafter raise the temperature to about 150° C. and initiate inert gas (e.g. nitrogen) sparge. Raise to about 175° C. during the next 2-hour period and heat soak at 175° C. for about 4 to 6 hours after which it can be readily filtered as shown in Example 2.

EXAMPLE 5

A lubricating oil composition was prepared for comparative testing of additives by blending together the individual components, noted below, usually at a slightly elevated temperature, i.e. from about 45° C. to above 65° C. to insure complete mixing. The final composition of Blend 5 formulated into a 10 W/30 SE quality automotive engine oil was as follows:

| Blend 5 Wt. % Active Ingredient | |
|---|---|
| Mineral Oil | 94.9 |
| Ashless Dispersant | 2.9 |
| Magnesium Sulfonate | 0.2 |
| ZDDP[(1)] | 0.9 |
| Rust-Inhibitor | 0.1 |
| Viscosity Index Improvers | 1.0 |
| Silicone Defoamer | 0.01 |
| Ashless Antioxidant | — |
| Metal Detergent-Inhibitor | — |

[(1)]Zinc dihydrocarbyl dithiophosphate such as zinc dinonyl phenol dithiophosphate This formulated blend was itself and in modified forms according to the teaching of this invention and the teaching of said Ser. No. 843,964 subjected to testing as hereinafter set forth:

1. Testing Procedure A

The Roxana Four-ball wear tester with the Brown/GE modification from Roxana Machine Works, St. Louis, MO was used to measure friction properties by the following procedure. The tester was assembled in the normal wear procedure as described in ASTM D2266-67 using four ½" bearing steel balls. The tester was brought to 110° C. and run at 1200 rpm and 15 kg for a minimum of 45 minutes. If the frictional force as seen on the strip chart recorder is constant for the last 10 minutes, the speed is reduced to 25 rpm. Otherwise, the test is carried on until frictional force has stabilized. The test at 25 rpm is carried out at 110° C. and 15 kg for 15 minutes or until frictional force has stabilized.

The compounds of the invention were then evaluated by subjecting the products to a study of their utility as a lubricity enhancing and/or antiwear additive for lubricating oils by using the Testing Procedure A. The weight percentage of amounts of molybdenum complex added is given in amount of complex added.

The results of tests under Procedure A are set forth in Table I.

From Table I, it is shown that the additive combination of the invention provides improved lubricity enhancement to lubricating oils when an active sulfur donor is present and that these three-component combinations of this invention have utility as additives for lubricating oils.

While the additive combination of this invention provides frictional performance to a fully formulated lubricating oil superior to that provided by the additive according to the teaching of said application Ser. No. 843,964, it is also much easier to filter and thereby remove unwanted and deleterious reaction byproducts than the products prepared according to the teachings of said Ser. No. 843,964, e.g. where a quantity of the former as shown by Example 2 filters through in less than 10 minutes a similar quantity of the latter would take from 0.5 to several hours (see Example 1 where it took in excess of 1 hour). In this regard, a solvent mixture of up to an equal amount of mineral oil with said alkanol solvent provides useful filtering ease of the solution reaction products.

Another advantage of said alkylphenol as a solvent for the reaction of the hydrocarbyl phenol sulfide and molybdenum compound, preferably molybdic oxide ($MoO_3$) resides in the enhanced reactivity of the components, i.e. shorter reaction times and/or more heat stable complexes when such a solvent is used as compared with mineral oil solvent. The heat stability of said complexes is enhanced by heating at from 160° to 190° C. for at least 4 hours, preferably 6 to 12 hours which in turn appears to impart increased antifriction activity to said complex-alkanol solution.

It is to be understood that the Examples present in the foregoing specification are merely illustrative of this invention and are not intended to limit it in any manner; nor is the invention to be limited by any theory regarding its operability. The scope of the invention is to be determined by the appended claims.

TABLE I

| Test | Added Mo Complex Example # | Added Mo Complex Wt (%) | Coefficient of Friction 46 cm/sec | Coefficient of Friction 1 cm/sec | Friction Reduction (%) 46 cm/sec | Friction Reduction (%) 1 cm/sec |
|---|---|---|---|---|---|---|
| 1 | — | — | 0.0835 | 0.1006 | — | — |
| 2 | 1 | 2.2 | 0.0436 | 0.0563 | 47.6 | 44.6 |
| 3 | 2 | 2.2 | 0.0478 | 0.0712 | 52.4 | 39.6 |
| 4 | 3 | 2.2 | 0.0361 | 0.0521 | | |
| 5 | 3 | 1.5 | 0.0404 | 0.0595 | | |

What is claimed is:

1. In a concentrate consisting essentially of one part by weight of an organo molybdenum complex obtained from a solution reaction of 1-2 moles of a $C_1$ to $C_{50}$ hydrocarbyl substituted thio-bis-phenol, 1-2 moles of an amine containing from 1 to 5 nitrogens and from 2 to 20 carbons and 1 molar equivalent of a source of molybdenum of the class consisting of molybdic trioxide, ammonium thiomolybdate, ammonium bismolybdate, molybdenum halides and ammonium tetrahydrate, the improvement of using from 0.25 to 5 parts by weight of an alkanol which contains from 5 to 50 carbons for the reaction solvent which is carried out at a temperature of from 135° C. to 225° C. whereby a more readily filterable reaction product is obtained.

2. A concentrate according to claim 1 wherein said alkanol contains from 8 to 18 carbons, said temperature is from 160° C. to 190° C. and carried out over a period of from 4 to 20 hours.

3. A concentrate according to claim 2 wherein said thio-bis-phenol is nonyl phenol sulfide, said molybdenum source is molybdic trioxide, said amine is ethylenediamine and said alkanol solvent is tridecyl alcohol present in an amount of about 1 part by weight.

4. A concentrate according to claim 2 wherein said alkanol is tridecyl Oxo alcohol.

5. A concentrate according to claim 1 wherein said complex is obtained as the product of a hydrocarbyl substituted thio-bis-phenol reacted with about 0.5 molar equivalent of the molybdic trioxide and one mole of an amine selected from the class of $C_6$-$C_{30}$ alkylamine, alkylene polyamines and their ethoxylated derivatives, alkanolamine, urea and ureides and dissolved in from 0.25 to 5 parts by weight of a $C_5$-$C_{50}$ alkanol solvent per part by weight of said product.

6. A hydrocarbon composition comprising a major portion of a hydrocarbon and at least a friction reducing amount of the combination of: (a) an organo molybdenum complex obtained from an alkanol solution reaction of 1-2 moles of a $C_1$ to $C_{50}$ hydrocarbyl substituted thio-bis-phenol, 1-2 moles of an amine reactant containing from 1 to 5 nitrogens and from 2 to 20 carbons and 1 molar equivalent of a source of molybdenum of the class consisting of molybdic trioxide, ammonium thiomolybdate, ammonium bismolybdate, molybdenum halides and ammonium tetrahydrate; (b) an oil-soluble active sulfur donor; and from 0.25 to 5 parts by weight of a $C_5$-$C_{50}$ alkanol per part by weight of said complex, said combination providing from about 0.005 to 0.2 weight percent molybdenum and said sulfur donor being present in at least 0.25 weight percent, all of said weight percent being based on the total weight of said composition.

7. A hydrocarbon composition according to claim 6 wherein said hydrocarbon is mineral oil, said organo complex is an oil-soluble reaction product of a hydrocarbyl substituted thio-bis-phenol with about 0.5 molar equivalent of the molybdic trioxide and one mole of ethylene diamine, said sulfur donor is an oil-soluble dihydrocarbyl ester of dithiophosphoric acid and said alkanol contains 8 to 18 carbons.

8. A hydrocarbon composition according to claim 7 wherein said mineral oil has a viscosity as measured by ASTM D-445 of about 2–40 centistokes at 99° C., said thio-bis-phenol is nonyl phenol sulfide, said molybdenum source if molybdic oxide, said active sulfur donor is zinc dihydrocarbyl dithiophosphate present in an amount of from 0.2–2 parts by weight per part by weight of molybdenum complex and said alkanol is tridecyl Oxo alcohol.

9. A method of preparing an organo molybdenum complex containing from about 0.5 to 5 wt.% nitrogen comprising the steps of reacting a $C_1$ to $C_{50}$ hydrocarbyl substituted thio-bis-phenol with about 0.5 molar equivalent of a molybdenum source of the class consisting of molybdic trioxide, ammonium thiomolybdate, ammonium bismolybdate, molybdenum halides, and ammonium heptamolybdate tetrahydrate and one mole of an amine containing from 1 to 5 nitrogens and from 2 to 20 carbons while dissolved in from 0.25 to 5 parts by weight of a $C_5$-$C_{50}$ alkanol solvent per part by weight of said product at a temperature of from about 145° C. to 225° C. for about 4 to 20 hours with at least 4 hours being above 160° C.

10. The method of claim 9 wherein said time of reaction is from 6 to 12 hours and at a temperature of from 160° C. to 190° C.

11. The method of claim 10 wherein said thio-bis-phenol is nonyl phenol sulfide, said alkanol is tridecyl alcohol and said amine is ethylene diamine.

12. A gasoline composition comprising gasoline containing from 10 to 1,000 parts per million based on the total weight of the gasoline composition of a molybdenum complex-alkanol solution obtained from the alkanol solution reaction of a $C_1$ to $C_{50}$ hydrocarbyl substituted thio-bis-phenol with about 0.5 molar equivalent of a molybdenum source of the class consisting of molybdic trioxide, ammonium thiomolybdate, ammonium bismolybdate, molybdenum halides, and ammonium heptamolybdate tetrahydrate and one mole of an amine containing from 1 to 5 nitrogens and from 2 to 20 carbons while dissolved in from 0.25 to 5 parts by weight of a $C_5$-$C_{50}$ alkanol solvent per part by weight of said complex.

* * * * *